United States Patent [19]

Sigel et al.

[11] 4,408,692
[45] Oct. 11, 1983

[54] STERILE COVER FOR INSTRUMENT

[75] Inventors: Bernard Sigel, Winnetka; Carolyn M. Semrow, Island Lake; Mark W. Kolstedt, Cary, all of Ill.; Edward J. Arkans, Sunland, Calif.; Lynn M. Kaczmarek, Park Ridge, Ill.

[73] Assignee: The Kendall Company, Boston, Mass.

[21] Appl. No.: 367,527

[22] Filed: Apr. 12, 1982

[51] Int. Cl.³ .................. B65D 85/16; B65D 83/00; A61I 17/02
[52] U.S. Cl. ................................. 206/438; 206/69; 206/303; 206/306; 53/390
[58] Field of Search ............... 206/438, 303, 306, 69; 53/390

[56] References Cited
U.S. PATENT DOCUMENTS

| 3,136,417 | 6/1964 | Clinch | 206/69 |
| 3,215,265 | 11/1965 | Welin-Berger | 206/63.2 |
| 3,301,394 | 1/1967 | Baermann et al. | 206/306 |
| 3,426,749 | 2/1969 | Jephcott | 128/11 |
| 3,431,706 | 3/1969 | Struk | 53/390 |
| 3,469,685 | 9/1969 | Baermann | 206/306 |
| 3,628,692 | 12/1971 | Blatz | 221/70 |
| 3,738,172 | 6/1973 | Sato | 73/343 |
| 3,746,159 | 7/1973 | May | 206/303 |
| 3,861,395 | 1/1975 | Taniguchi | 128/349 |
| 4,101,031 | 7/1978 | Cromie | 206/438 |

Primary Examiner—William T. Dixson, Jr.
Attorney, Agent, or Firm—Powell L. Sprunger

[57] ABSTRACT

A sterile cover for an instrument comprising, a tray having an upright post, with the post having an upper end and a lower end. The cover has a sleeve of flexible material having an open end and a closed end. The sleeve is placed on the post with the closed end being located adjacent the upper end of the post, with the sleeve extending over the post from the upper end toward the lower end of the post, and with the open end of the sleeve being accessible to a user to remove the sleeve from the post.

11 Claims, 4 Drawing Figures

U.S. Patent     Oct. 11, 1983     4,408,692
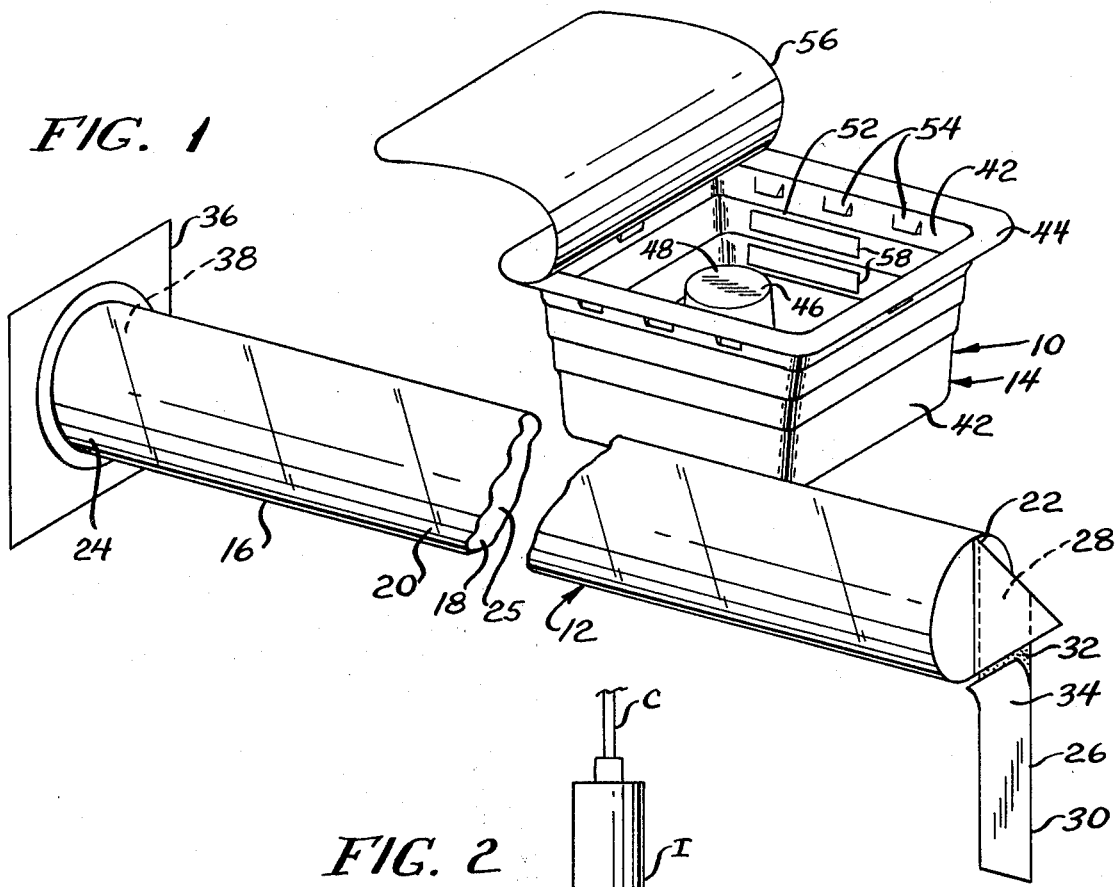
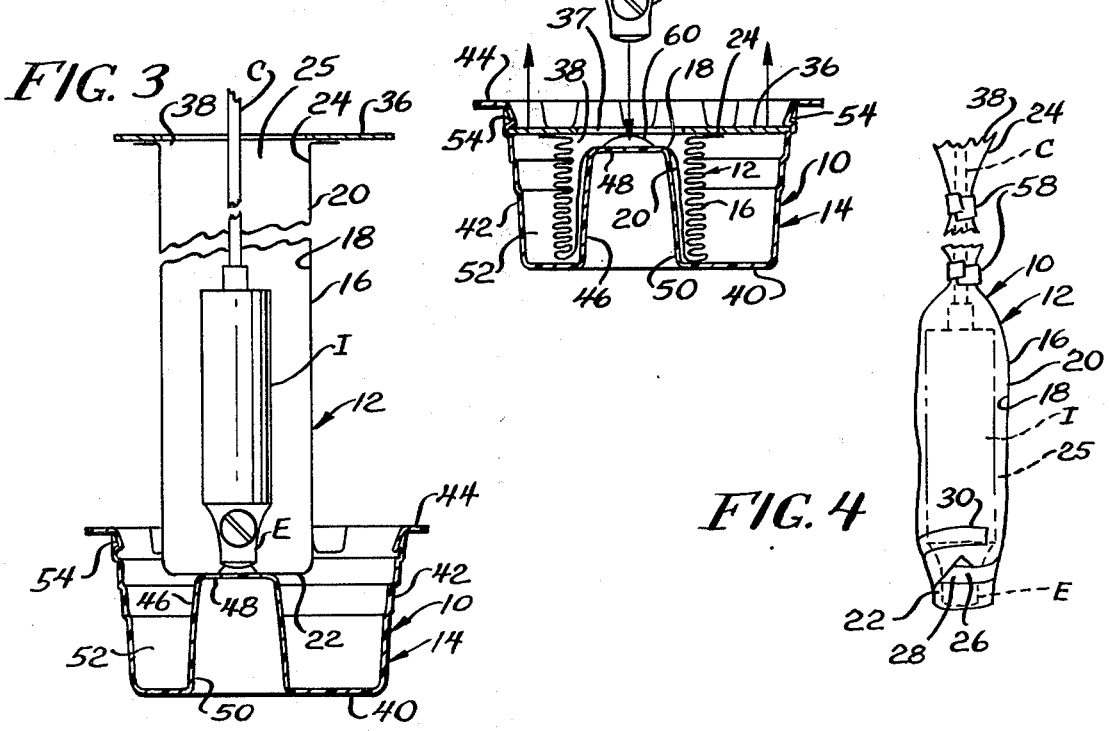

STERILE COVER FOR INSTRUMENT

BACKGROUND OF THE INVENTION

The present invention relates to a sterile cover for an instrument.

Before the present invention, various instruments, such as an ultrasound probe, have been utilized during medical procedures. For example, the ultrasound probe may be utilized to view tumors in the abdominal cavity. Accordingly, it may be desirable to introduce the probe into the abdominal cavity, but typically the probe would be non-sterile and its introduction could cause contamination to the patient.

SUMMARY OF THE INVENTION

A principal feature of the present invention is the provision of an improved cover for an instrument.

The sterile cover of the invention comprises a tray having an upright post, with the post having an upper end and a lower end. The cover has a sterile sleeve of flexible material having an open end and a closed end. The sleeve is placed on the post with the closed end being located adjacent the upper end of the post, with the sleeve extending over the post from the upper end toward the lower end of the post, and with the open end of the sleeve being accessible to a user.

A feature of the present invention is that an outer end of the instrument may be placed over the sleeve at the upper end of the post, and the sleeve may be removed from the post while placing it over the instrument.

Another feature of the invention is that the sleeve covers the instrument, and thus provides a sterile cover for the non-sterile instrument.

Yet another feature of the invention is that the sleeve may have a panel secured to the open end of the sleeve, and the tray may hold the panel in place adjacent the upper end of the post at a convenient location for access of the open end of the sleeve to the user.

A further feature of the invention is that the sleeve may be secured in place on the instrument by one or more tape strips.

Yet another feature of the invention is that the sleeve may have a rupturable capsule of gel adjacent the upper end of the post for use on the instrument.

Still another feature of the invention is that the tray may be closed by a cover sheet in order to maintain the contents of the tray in a sterile condition.

Further features will become more fully apparent in the following description of the embodiments of this invention and from the appended claims.

DESCRIPTION OF THE DRAWINGS

In the drawings:

FIG. 1 is a fragmentary perspective view of a sterile cover of the invention for a non-sterile instrument comprising an elongated sleeve, and a tray;

FIG. 2 is a sectional view showing the sleeve gathered on a post of the tray;

FIG. 3 is a fragmentary sectional view illustrating the sleeve as unwrapped from the post about the instrument; and FIG. 4 is a fragmentary plan view illustrating the sleeve as secured about the instrument.

DESCRIPTION OF THE PREFERRED EMBODIMENTS

Referring now to FIGS. 1 and 2, there is shown a sterile cover generally designated 10 for a non-sterile instrument I, such as an ultrasound probe, comprising an elongated sterile sleeve 12 and a tray 14. The sleeve 12 comprises an elongated cylindrical wall 16 of flexible plastic material having an inner surface 18, an outer surface 20, a closed end 22, an opposed open end 24, and a cavity 25. In a preferred form, the closed end 22 may be tapered, and a tape strip 26 may extend from the closed end 22 of the sleeve 12. The tape strip 26 may have one end 28 secured to the closed end 22 of the sleeve 12, and the other end 30 of the strip 26 may have adhesive 32 releasably covered by a release sheet 34. The sleeve 12 may have a panel 36 of relatively stiff material, such as cardboard, secured to the open end 24 of the sleeve 12, and extending around an opening 38 of the sleeve 12, with the panel 36 having an opening 37 in registration with the sleeve opening 38.

The tray 14 has a bottom wall 40, and a plurality of sidewalls 42, such as four, extending upwardly from opposed sides of the bottom wall 40. As shown, the sidewalls 42 may have an outwardly directed rim 44 at an upper end of the sidewalls 42. The tray 14 has a central post 46 extending upwardly from the bottom wall 40, with the post 46 having a flat upper end 48, and a lower end 50 connected to the bottom wall 40. As shown, the sidewalls 42 and bottom wall 40 define a cavity 52 in the tray 14. The tray sidewalls 42 may have a plurality of inwardly directed lips 54 at a location slightly above the upper end 48 of the post 46. The tray 14 may also have a cover sheet 56 of flexible bacteria impervious material releasably attached to the rim 44 in order to maintain the contents of the cavity 52 in a sterile condition. The tray 14 may have one or more tape strips 58 releasably attached to a surface of the sidewalls 42. The tray 14 may be constructed of a suitable plastic material.

With reference to FIG. 2, the sleeve 12 is placed over the post 46 with the closed end 22 of the sleeve 12 located adjacent the upper end 48 of the post 46, and with the inner surface 18 of the sleeve 12 being exposed from the upper end 48 of the post 46. The wall 16 of the sleeve 12 extends from the upper end 48 of the post 46 toward the lower end 50 of the post 46, and the sleeve wall 16 is gathered into a configuration of reduced dimensions around the post 46. As shown, the open end 24 of the sleeve 12 is located adjacent the upper end 48 of the post 46 such that it is accessible to the user. The panel 36 has a configuration approximately the shape of the inside of the tray sidewalls 42, and the panel 36 is located beneath the lips 54 of the tray 14 where the lips 54 frictionally engage the upper surface of the panel 36 in order to prevent outward movement of the sleeve 12 and retain the open end 24 of the sleeve 12 in place at a location slightly above the upper end 48 of the post 46. As shown, the sleeve 12 may have a rupturable capsule 60 of coupling gel for the instrument I at a location on the inner surface 18 of the sleeve 12 above the flat upper end 48 of the post 46.

In use, the cover sheet 56 is removed in order to expose the contents of the tray 14. The outer end E of the elongated and non-sterile instrument I may then be placed over the capsule 60 of gel, and the instrument I may be pressed against the capsule 60 in order to rupture the capsule 60 and place the gel on the end E of the instrument I. With the instrument retained in this position, the panel 36 may be grasped by the user, and may be removed from the lips 54 of the tray 14. As shown in FIG. 3, the panel 36 is then raised over the instrument I in order to raise the open end 24 of the sleeve 12 over the instrument I, thus removing and ungathering the folded sleeve wall 16 from the post 46 while the portion of the sleeve 12 located over the upper end 48 of the post 46 remains in place. In this manner, the sleeve 12 is removed from the post 46 into a raised configuration, with the sleeve 12 covering the instrument I and the instrument cord C, such that the instrument I is received in the sleeve cavity 25.

Next, with reference to FIG. 4, the panel 36 is removed from the sleeve 12. The tapered portion of the sleeve closed end 22 is then folded over an adjacent portion of the sleeve 12, after which the release sheet 34 is removed from the tape strip 26 in order to expose the adhesive 32. The tape strip 26 is tightly wrapped around the end E of the instrument I, and the strip 26 is secured in place in order to snugly gather the closed end 22 of the sleeve 12 about the instrument I and retain it in place. Also, the tape strips 58 may be removed from the tray 14, and may be secured about the sleeve 12 in a gathered configuration of the sleeve 12 about the cord C in order to retain the sleeve 12 in place on the instrument I and cord C.

Thus, in accordance with the present invention, the sterile sleeve 12 may be readily removed from the tray 14, and may be placed about the instrument I in order to place a sterile cover over the non-sterile instrument I and cord C. In this manner, the sterile device may be introduced into a cavity of a patient, such as the abdominal cavity, without the risk of contamination to the patient.

The foregoing detailed description is given for clearness of understanding only, and no unnecessary limitations should be understood therefrom, as modifications will be obvious to those skilled in the art.

We claim:

1. A sterile cover for an instrument, comprising:
 a tray having an upright annular post, with the post having an upper end and a lower end; and
 a sleeve of flexible material having an open end and a closed end, said sleeve being placed on the post with the closed end being located adjacent the upper end of the post, with said sleeve extending over the post around the post from the upper end toward the lower end of the post, and with the open end of the sleeve being located adjacent the upper end of the post and being accessible to a user to remove the sleeve from the post.

2. The cover of claim 1 wherein the sleeve is gathered into a configuration of reduced dimensions over the post.

3. The cover of claim 1 wherein the upper end of the post is flat.

4. The cover of claim 1 including at least one tape strip attached to the tray.

5. The cover of claim 1 including a rupturable capsule of gel on the inside of the sleeve overlying the upper end of the post.

6. The cover of claim 1 wherein the tray has sidewall means defining a cavity surrounding the post.

7. The cover of claim 6 including a cover sheet secured to an upper portion of the sidewall means and closing the cavity.

8. The cover of claim 6 including a panel of relatively stiff material secured to and surrounding the open end of the sleeve, and means for releasably attaching the panel to the sidewall means.

9. The cover of claim 8 wherein the attaching means comprises a plurality of lips on the sidewall means engaging the panel.

10. The cover of claim 1 wherein the closed end of the sleeve is tapered.

11. The cover of claim 1 including an elongated tape strip extending from the sleeve at a location adjacent the closed end, said strip having adhesive and a release sheet releasably covering adhesive on the strip.

* * * * *